(12) United States Patent
Quinn

(10) Patent No.: US 7,625,345 B2
(45) Date of Patent: Dec. 1, 2009

(54) MOTIVATIONAL SPIROMETRY SYSTEM AND METHOD

(75) Inventor: David E. Quinn, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 284 days.

(21) Appl. No.: 11/079,714

(22) Filed: Mar. 14, 2005

(65) Prior Publication Data
US 2006/0206036 A1 Sep. 14, 2006

(51) Int. Cl.
A61B 5/08 (2006.01)
A63B 23/18 (2006.01)

(52) U.S. Cl. .................... 600/538; 600/529; 482/13
(58) Field of Classification Search ............. 482/13; 600/538
See application file for complete search history.

(56) References Cited

U.S. PATENT DOCUMENTS

| 3,896,792 | A | | 7/1975 | Vail et a. |
| 4,296,756 | A | * | 10/1981 | Dunning et al. ............. 600/529 |
| 4,984,158 | A | | 1/1991 | Hillsman |
| 5,137,026 | A | | 8/1992 | Waterson et al. |
| 5,167,506 | A | | 12/1992 | Kilis et al. |
| 5,267,942 | A | | 12/1993 | Saperston |
| 5,318,038 | A | | 6/1994 | Jackson et al. |
| 5,333,106 | A | | 7/1994 | Lanpher et al. |
| 5,431,154 | A | | 7/1995 | Seigel et al. |
| 5,549,117 | A | * | 8/1996 | Tacklind et al. ............. 600/529 |
| 5,564,432 | A | | 10/1996 | Thomson |
| 5,827,179 | A | | 10/1998 | Lichter et al. |
| 6,083,141 | A | | 7/2000 | Hougen |
| 6,167,362 | A | | 12/2000 | Brown et al. |
| 6,468,211 | B1 | | 10/2002 | Binder |
| 6,508,772 | B2 | | 1/2003 | Vilozni |
| 2001/0003144 | A1 | * | 6/2001 | Vilozni ....................... 600/538 |
| 2003/0000522 | A1 | * | 1/2003 | Lynn et al. ............. 128/200.24 |

OTHER PUBLICATIONS

Yemenijian, Debra; "2004 Spirometry Buyers Guide".
The Nagel Network, Inc; "PC Based Spirometers"; printed from www.nagelnetwork.com/pcspir.html on Feb. 1, 2005.
Numed; "Microloop Spirmeter"; printed from www.numed.co.uk/microloop. html on Feb. 1, 2005.
Micro-Direct; "The New NicroLab 3500 Spirometer"; printed from www.mIcro-direct.com/microlab.html on Feb. 1, 2005.
Micro-Direct; "Spiro USB Spirometer"; printed from www.micro-direct.com/spiro USB.html on Feb. 1, 2005.
Micro-Direct; "Spida 5"; printed from www.micro-direct.com/spida. html on Feb. 15, 2005.
Micro Medical Ltd; "Spida 5"; Product brochure; printed from www.micromedical.co.uk on Feb. 1, 2005.
Welch Allyn, Inc.; Spirometer Product Brochure, copyright 2003.

* cited by examiner

Primary Examiner—Patricia C Mallari
(74) Attorney, Agent, or Firm—Hiscock & Barclay, LLP

(57) ABSTRACT

A method is disclosed for motivating a user of a spirometry system 20 having a display screen 12, an air-tube 22, a flow measurement sensor 24 operatively associated with the air-tube 22, a display screen 26, and an associated processor 30. A motivational animation is displayed on the display screen 12 having a first aspect that reflects a relative evaluation of a determined peak flow rate to a goal value therefor and having a second aspect that reflects a relative evaluation of a determined total flow volume to a goal value therefor. The processor 30 repeatedly updates the motivational animation during the period of use of the spirometer to reflect the degree of achievement of both of the goal values by the user.

4 Claims, 15 Drawing Sheets

| Patient Name | | Date / Time |

Spirometry Settings

1. Operation Settings
2. Calibration Settings
3. Screen Settings
4. Print Settings
5. Patient Data Settings
6. Edit Interpretation List
7. Communication Settings
0. Previous Menu Type a number or use arrow keys to make your selection

| ↓ | ↑ | ← | → | |

FIG. 4

| Patient Name | | Date / Time |

Spirometry Operation Settings

1. Select Adult Predictive Norm
2. Select Pediatric Predictive Norm
3. Define Best Effort
4. Define Reversibility Formula
5. Define FEV1% Formula
6. Enable Predictive Points
7. Enable Predictive Curve
8. Enable ATS Acceptability Criteria
9. Enable ATS Interpretive Results
A. Insert Composite Norm Values
0. Previous Menu Type a number or use arrow keys to make your selection

| ↓ | ↑ | ← | → | |

FIG. 5

| Patient Name | | Date / Time |
|---|---|---|

Spirometry Operation Settings

1. Select Adult Predictive Norm
2. Select Pediatric Predictive Norm
3. Select Best Effort
4. Select Reversibility Formula
5. Select FEV1% Formula
6. Enable Predictive Points
7. Enable Predictive Curve
8. Enable ATS Acceptability Criteria
9. Enable ATS Interpretive Results
A. Insert Composite Norm Values
0. Previous Menu Berglund 1963
Crapo 1981
ECCS / Quanjer 1993
Gulsvik 2001
Hedenström 1986
Knudson 1976
Knudson 1983
Kory 1961
Morris 1971
NHANES III 1999 [Default]
Schoenberg 1978
Viljanen 1981

Choose your adult predictive norm.

| Patient Name | | Date / Time |
|---|---|---|

Spirometry Operation Settings

1. Select Adult Predictive Norm
2. Select Pediatric Predictive Norm
3. Select Best Effort
4. Select Reversibility Formula
5. Select FEV1% Formula
6. Enable Predictive Points
7. Enable Predictive Curve
8. Enable ATS Acceptability Criteria
9. Enable ATS Interpretive Results
A. Insert Composite Norm Values
0. Previous Menu Berglund 1963
Dockery 1983
Hsu 1979
Knudson 1976
Knudson 1983 [Default]
Koillinen 1998
NHANES III 1999
Polgar 1971
Schoenberg 1978
Solymar 1980
Zapletal 1981

Choose your pediatric predictive norm.

MOTIVATIONAL SPIROMETRY SYSTEM AND METHOD

BACKGROUND OF THE INVENTION

The present invention relates generally to breathing therapy and, more particularly to a motivational spirometry system and method for motivating a user during use of a spirometry system.

Spirometers are Lung function measurement devices used to measure the flow of air exhaled or inhaled by a user of the device. The peak flow rate measured during a period of use and the total air flow volume measured during a period of use are measurements that are indicative of the pulmonary capabilities of a patient. These measurements are useful to medical personnel both in diagnostic analysis and in treatment of a patient.

Spirometry systems are now in common use in hospitals, doctor's offices, clinics and rehabilitation facilities as Lung function measurement devices. Typically, these systems include a flow sensor and associated processor software. The flow sensor includes an air tube device having a mouthpiece at one end and a sensor for measuring the flow of air through the air tube. The flow sensor is connected to a processor into which the associated software has been programmed for processing the flow measurements received from the sensor during the period of use, that is the period of time during which the patient is exhaling or inhaling directly through the air tube. In use, the patient places her/his mouth securely around the mouthpiece and exhales or inhales through the air tube as hard and as long as she/he can without interruption. The patient then repeats the process as directed by the responsible medical personnel. Spirometry systems are commercially available in which the processor and the flow sensor are integrated into a stand-alone unit that includes a display, for example a backlit graphical display screen, on which test results may be displayed in real-time. Spirometry systems are also commercially available in which the processor is a computer, either main-frame or personal, such as desktop or laptop PC, having a data port into which the flow sensor is connected. The associated software is loaded into the computer and the test results displayed in real-time on the computer's display screen.

Lung function measurement using spirometers can be particularly challenging in children, particularly young children. It has been appreciated in the art that providing stimulating feedback to the users of a spirometer, such as in particular children, may improve the accuracy and quality of the child's effort. For example, in U.S. Pat. No. 5,333,106, Lanpher et al. disclose providing stylized cartoon feedback on the graphic display screen of the spirometer system, or modulated auditory feedback or verbal feedback to the user. In U.S. Pat. No. 6,508,772, Vilozni discloses using a computer game presented on the display screen associated with the spirometer for stimulating the performance of a pre-school child or other subject of limited comprehension during breathing therapy. Vilozni notes that it is particularly advantageous to structure the game as a short story having a surprise ending.

Spirometers are presently commercially available that include animated displays depicting teddy bears blowing out the candles on a cake, depicting a boy blowing bubble gum bubbles, or depicting a boy drinking a milk shake from a glass through a straw. When using such spirometers, the patient is instructed to exhale as hard as possible in order to extinguish the candles or break the bubble gum bubble. However, such animated displays reflect the user's success relative to only one performance measure, typically either forced vital capacity (FVC) or peak Expiratory flow (PEF).

SUMMARY OF THE INVENTION

It is an object of the present invention to provide an improved method for motivating a user when performing a spirometry effort using a spirometry system having an associated display.

It is an object of a one aspect of the present invention to provide a method for motivating a user to improve both peak flow rate and total volume, expired or inspired, when performing a spirometry exercise using a spirometry system having an associated display.

It is an object of a further aspect of the present invention to provide an apparatus for motivating a user to improve both peak flow rate and total volume, expired or inspired, when performing a spirometry exercise using a spirometry system having an associated display.

In one aspect of the invention, a method is provided for operating a spirometry system to motivate a user to improve breathing performance, comprising the steps of: measuring a flow of air generated by a user during a period of use of the spirometer apparatus, processing the measurements to determine a peak flow rate and a total flow volume, evaluating the determined peak flow rate relative to a normative value therefor, and evaluating the determined total flow volume relative to a normative value therefor; and generating a motivational animation having a first aspect that reflects the relative evaluation of the determined peak flow rate to the normative value therefor and having a second aspect that reflects the relative evaluation of the determined total volume to the normative value therefor.

The method may include the further step of displaying the motivational animation to the user continuously during the period of use of the spirometer apparatus and repeatedly updating the motivational animation display during the period of use of the spirometer apparatus. Advantageously, the motivational animation displays a fireman spraying water at a fire, wherein the magnitude of water flow sprayed at the fire reflects the relative evaluation of the determined peak flow rate to the normative value therefor and the degree of fire extinguished reflects the relative evaluation of the determined total volume to the normative value therefor.

The method may also include the step of selecting the normative values for peak flow rate and total volume based on the demographics of the user and normative parameters from a clinical population study, and, advantageously, selecting the normative values based on at least one of the age, sex, height and weight of the user. The method may also include the step of selecting the normative values for peak flow rate and total flow volume based on the expected performance of the user or on the past performance of the user.

The method may also include the step of allowing the clinician to increase or decrease the target values for peak flow and total volume by actuating buttons or keys on the device to make achieving the goals of the animation easier or more difficult.

BRIEF DESCRIPTION OF THE DRAWINGS

FIG. 4 shows a sample menu display of spirometry settings options;

FIG. 5 shows a sample menu display of spirometry operation settings;

FIG. 6A shows a sample menu display of available adult predictive norms;

FIG. 6B shows a sample menu display of available pediatric predictive norms;

DETAILED DESCRIPTION OF THE INVENTION

Figure 1:
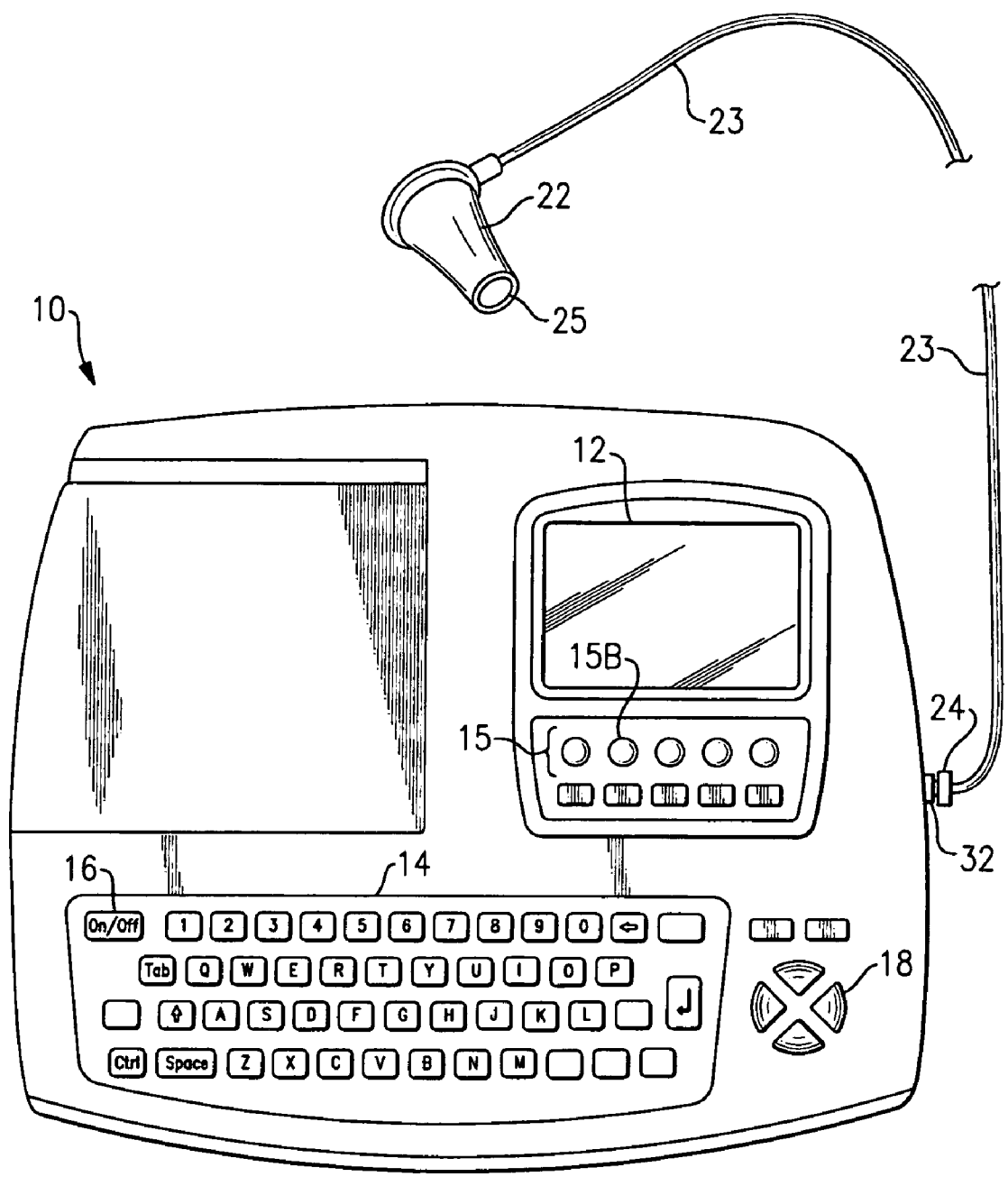
FIG. 1 is a plan view of a stand-alone embodiment of the spirometry apparatus of the present invention.

Referring now to FIG. 1, a spirometry system in accordance with the present invention is shown integrated in a patient evaluation workstation 10. The workstation 10 may include other patient evaluation systems, such as for example an electrocardiograph, which operate independently of the spirometry system of the present invention and are not pertinent to the discussion of the present invention. The workstation 10 includes a display screen 12 with associated function buttons 15, an alphanumeric keyboard 14, an on/off switch 16 and a multi-direction arrow key pad 18. Although shown incorporated into a patient evaluation workstation for purposes of illustration, it is to be understood that the spirometry system of the present invention is not limited in application to the depicted embodiment. For example, the spirometry system of the present invention may also be embodied as a stand-alone patient evaluation device or associated with a personal computer, whether desk-top, or portable, or main frame computer network.

Figure 2:
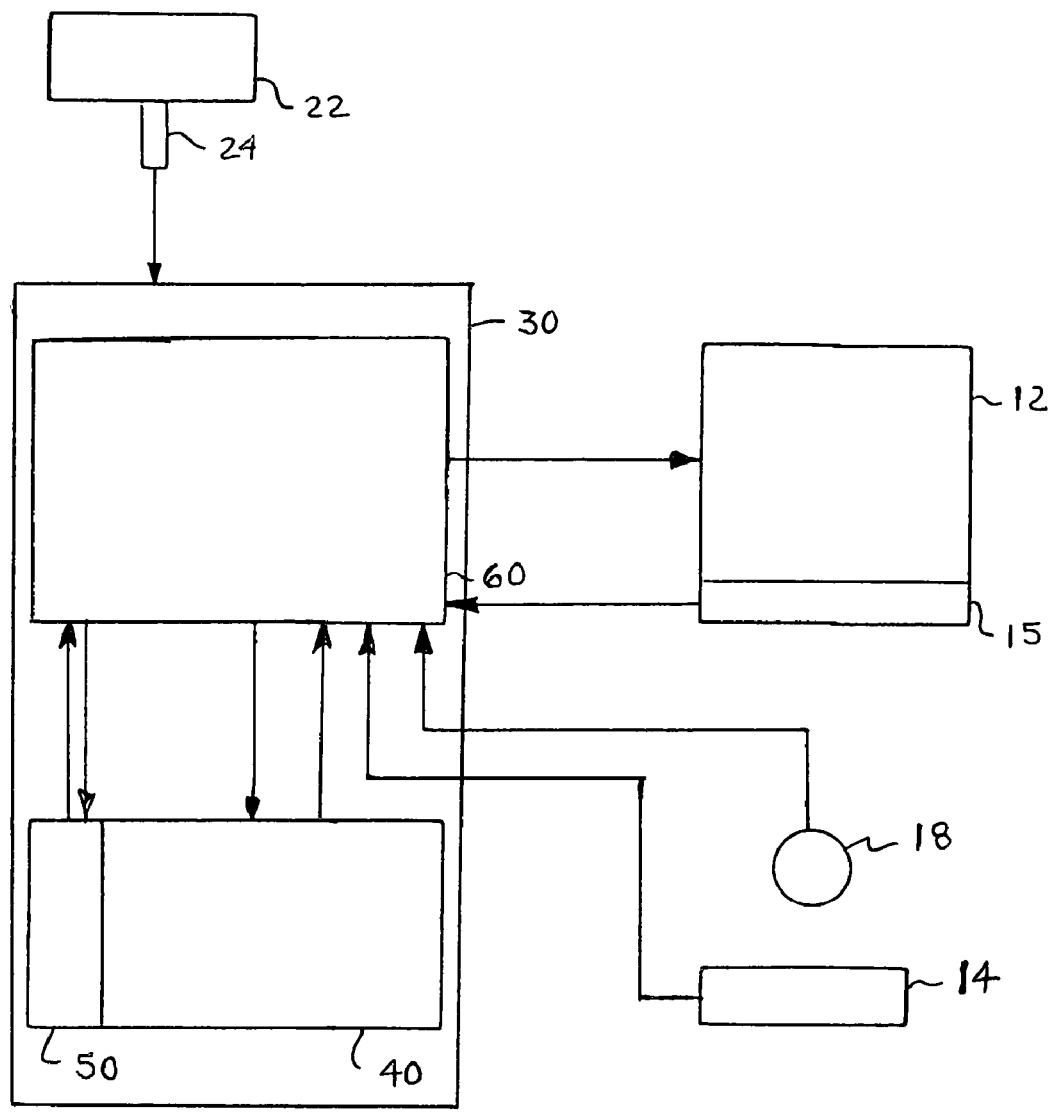
FIG. 2 is a block diagram illustrating the spirometry apparatus of the present invention.

Referring now to FIGS. 1 and 2, the spirometry system 20 includes an air-tube 22, a flow measurement sensor 24 operatively connected to the air-tube 22 by flow tubing 23, a display screen 26, and an associated processor 30. The air-tube 22 may be of conventional design having a mouthpiece 25 adapted to be received into the mouth of the user for exhaling or inhaling air flow therethrough induced by the user. The flow measurement sensor 24 is disposed at the distal end of the flow tubing 23 and connected to the processor 30, for example to a RS-232 serial port 32 associated with the processor 30. Alternatively, if desired, the flow measurement sensor 24 may be provided with an appropriate transmitter and the processor 30 with a compatible receiver for providing wireless communication between the flow measurement sensor 24 and the processor 30. Any type of flow measurement sensor may be used that produces a signal proportional to the induced air flow through the air-tube 22. For example, the flow measurement sensor may comprise a fixed orifice device with pressure transducer and an associated analog-to-digital signal converter. Advantageously, the air-tube, pressure tubing assembly and flow sensor assembly may comprise a Model D9w spirometer unit commercially available from Medikro OY of Kuopio, Finland, which is equipped with a Medikro model M9228 pressure transducer and Medikro Model M9220 flow tubing.

The processor 30 includes a system memory 40 including an image buffer 50, and a control circuit 60 having conventional electronics for receiving various inputs, including measurement data from the sensor 24, for processing air flow measurement data generated by the flow measurement sensor 24, and controlling various outputs, including the displays presented to the user on the display screen 12. The control circuit 60 may include a controller and a central processing unit and is in communication with the system memory 40. The system memory 40 is adapted to receive and store pre-installed information, such as for example normative performance parameters from one or more clinical population studies, inputted information, such as demographics of the test subject and desired performance parameters, and test results for the test subject, both prior and concurrent. The system memory 40 may include such as elements as RAM, EROM, EPROM and FLASH memory. The image buffer 50 is adapted to store a plurality of pre-installed motivational animation images to be selectively display on the display screen 12 in a manner to be further described hereinafter.

In the method of the present invention, motivational animation images are selectively displayed on the display screen 12 in response to the real-time performance of the test subject using the spirometry apparatus 20. The method of the present invention includes the steps of measuring a flow of air generated by a user during a period of use of the spirometry system, processing the measurements to determine a peak flow rate and a total flow volume, evaluating the determined peak flow rate relative to a normative value therefor, and evaluating the determined total flow volume relative to a normative value therefor; generating a motivational animation having a first aspect that reflects the relative evaluation of the determined peak flow rate to the normative value therefor and having a second aspect that reflects the relative evaluation of the determined total flow volume to the normative value therefor.

Figure 3:
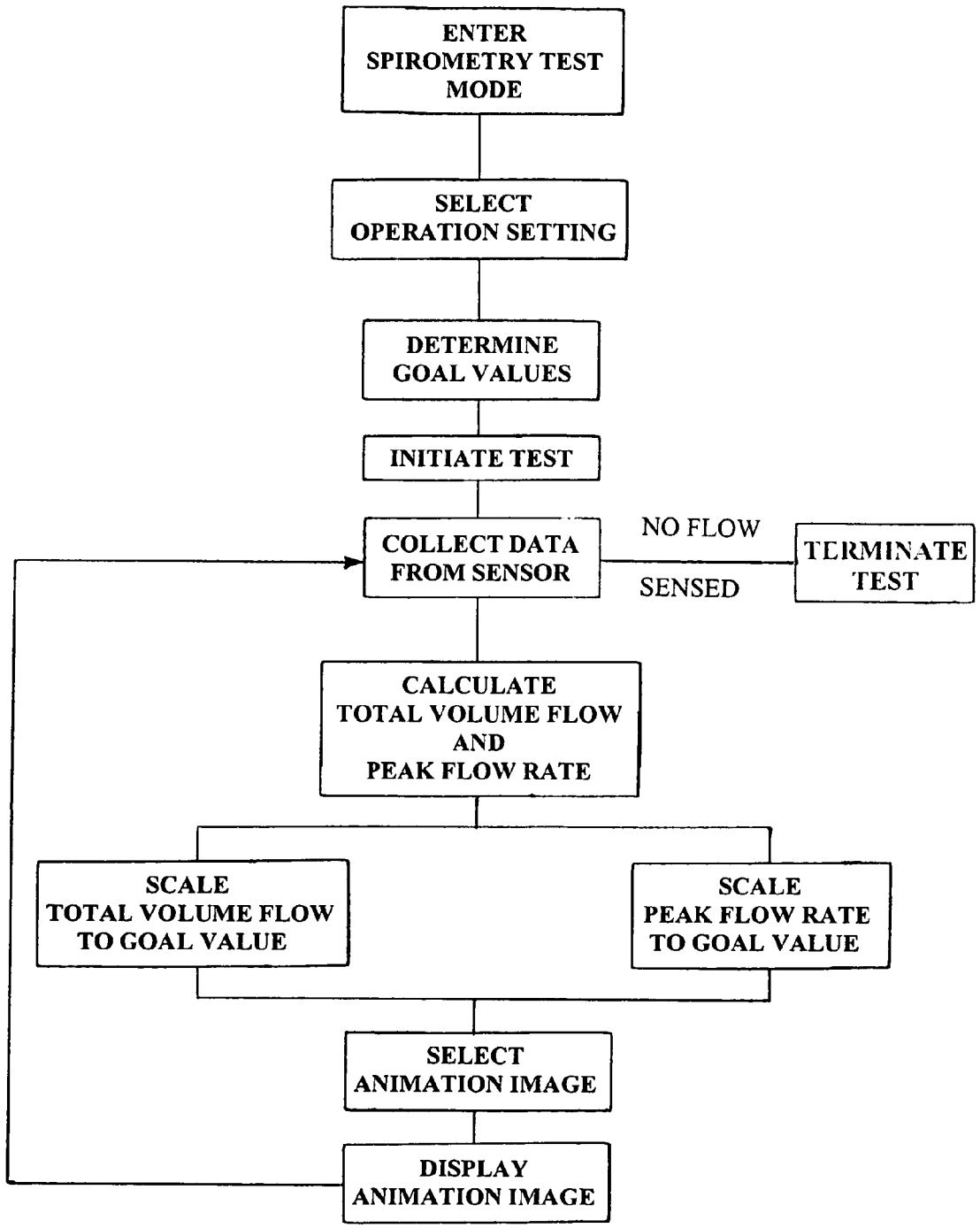
FIG. 3 is a block diagram illustrating the method of the present invention.

Referring now to FIG. 3, prior to beginning a spirometry test, the operator selects "Spirometry Settings" from a main menu on the display screen 12 or otherwise elects to enter the spirometry test mode, for example by pressing the spirometer function button 15B on the workstation 10. In response thereto, the processor 30 checks to verify that the spirometry flow measurement sensor 24 is indeed operatively connected to and in communication with the processor 30. If not, the processor will display "No Spirometer Found", thus prompting the operator to take corrective action. With the sensor 24 operative, the processor 30 will display a Spirometry Settings menu, such as illustrated in FIG. 4, on the display screen 12.

When the operator selects a particular option from the Spirometry Settings menu, the name of the option will appear on the status screen. For example, the operator will select the Spirometry Operation Settings to select the normative parameter that will be used for the upcoming test. In response thereto, the processor 30 will cause a display representing the available operational settings, such as for example as illustrated in FIG. 5. The operator now has the option of selecting the particular normative reference that will be used in calculating the test subjects relative performance versus the selected normative reference. If the operator selects the Adult Predictive Norm option, the processor 30 will display a plurality of options on the display screen 12, such as for example illustrated in FIG. 6A, each option identifying a particular clinical study accepted in the medical field as a valid adult normative study, one of which may be identified as a default option. If the operator selects the Pediatric Predictive norm option, the processor 30 will display a plurality of options on the display screen 12, such as for example illustrated in FIG. 6B, each option identifying a particular clinical study accepted in the medical field as a valid pediatric normative study, one of which may be identified as a default option. The studies identified in FIGS. 6A and 6B are merely representative of available clinical studies and are illustrated solely for purposes of illustration.

Instead of selecting a particular norm study, the operator may instead select "Best Effort" from the Spirometry Operation Settings menu. If this option is selected, the performance of the test subject is measured against prior performance rather than a normative value from a clinical study. In response to selection of the Best Efforts option, the processor 30 will display two options for calculation of best effort: Best Measurement or Best Composite. If Best Measurement is selected, the performance of the test subject will be compared against the calculated total volume and the calculated peak flow rate from the best prior test for the test subject, the best test being the having the highest sum of total flow volume and peak flow rate values. If Best Composite is selected, the performance of the test subject will be compared against individual composite valves of all or the last so many tests preceding the upcoming test. For either option, the processor 30 will calculate the appropriate goal values using prior test data for the test subject, that prior data having been stored by the processor 30 is the data storage memory 40.

The operator may also select the "Insert Composite Norm Values" to directly input a set of individual performance norms that the operator desires the test subject to achieve. This allows the attending medical staff to personalize the performance scaling to a particular test subject. For example, the operator may select particular normative references from various clinical studies, rather than selecting all from a single clinical study. The remaining options on the Spirometry Operation Settings menu are self-explanatory to those skilled in the art and are not germane to understanding the present invention.

When using clinical studies for selecting the predictive normative parameters, the processor 30 will use demographical information relating to the particular test subject, including for example but not limited to age, height, weight, sex, etc., to select the particular goal values for total volume flow and peak flow rate for the test subject based on the selected study installed in the data storage memory. If Best Efforts has been selected, the processor 30 will set the goal values equal to the test subjects best measurement or best composite values, as selected, as total volume flow and peak flow rate. If specific desired goals have been input for the test subject, the processor 30 will simply set the goal values for total volume flow and peak flow rate to the respective inputted values therefor. The goal values for total flow volume and peak flow rate having been established, the test subject may now initiate a test by exhaling into the air-tube as hard as and as long as the test subject is able.

During a test, the processor 30 continuously receives flow measurement signals form the flow measurement sensor 24. Every 100 milliseconds, the processor 30 calculates the current value for the total volume flow (FVC) to that time in the test and the current peak flow rate (PEF). The processor 30 also scales the performance of the test subject to the goal values for total volume flow and peak flow rate every 100 milliseconds. The scaled values are expressed as a percentage of the respective goal values according to the following formulas:

% Expected $PEF$=(Current $PEF$ value/$PEF$ Goal value)*100

% Expected $FVC$=(Current $FVC$ value/$FVC$ Goal value)*100.

To provide optimal incentive to encourage test subjects to both deliver a powerful blow, i.e. maximize peak flow rate, and to empty their lungs, i.e. maximize total volume flow, the present invention provides a real-time motivational animation having two aspects, one of which varies in response to the scaled values for PEF and the other of which varies in response to the scaled values for FVC. Further, the motivational animation is adapted to encourage an increasing powerful blow and a sustained expiration. The initial goals may be scaled up or down after or while the clinician observes the test subject's performance and ability.

In the embodiment of the present invention described herein, the motivational animation displayed on display screen 12 during a test depicts an animation of a fireman spraying water from a hose in the direction of a fire, in this embodiment a house fire. In this animation, water is initially merely dripping from the hose held by the fireman, while a number of fires burn on the burning house. The goal of the animation is to extinguish all of the fires. To accomplish this goal, the test subject must achieve the goal values for both peak flow rate and total volume flow determined as hereinbefore described for that particular test subject. The magnitude of and distance that the water flow extends to the house is directly related to achievement of the peak flow rate goal. For water from the hose to reach the fires, the test subject must achieve a peak flow rate equal to or greater than a preset percentage of goal value for peak flow rate. Once that preset percentage of the goal value for peak flow rate is achieved, the water flowing from the hose in the animation reaches the fires. The degree of the fire extinguished is directly related to achievement of the goal value for total volume expelled for the particular test subject once the water flow has reached the fire in the animation. When the test subject achieves a preset percentage of the goal value for the total volume, all fires on the animation are completely extinguished and a congratulatory message, such as "Good Job" is displayed across the screen display 12.

Figure 7A:
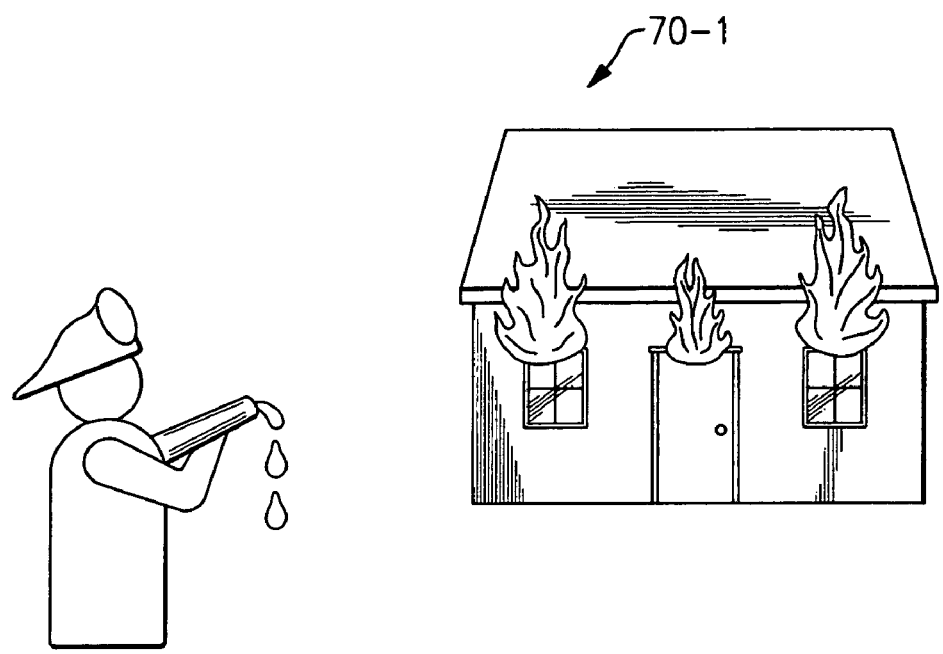
FIGS. 7A & 7B show a first set of paired animation images.
Figure 7B:
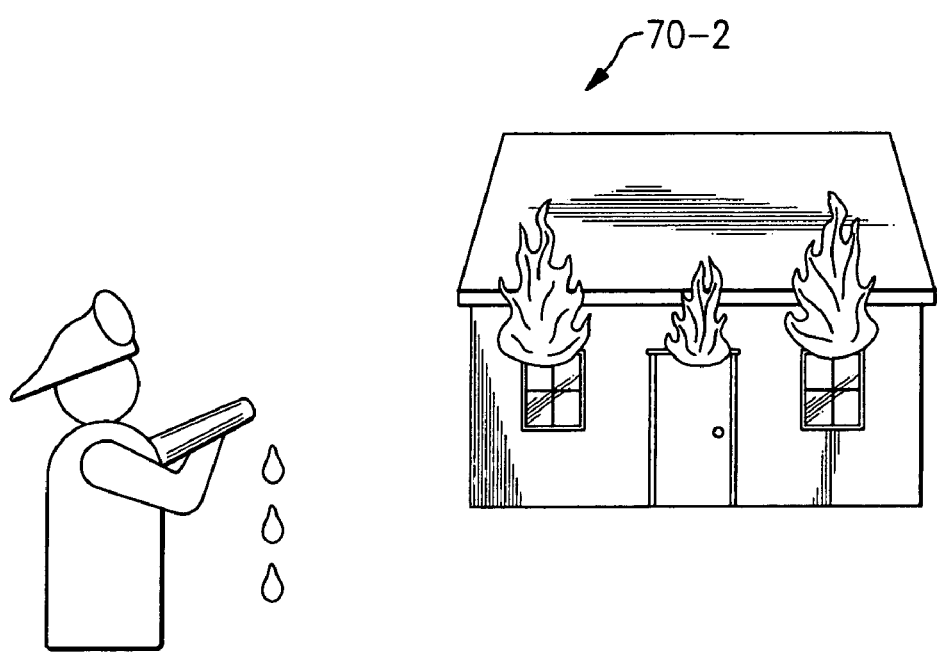

Referring now to FIGS. 7A, B through-15A,B, an exemplary fireman extinguishing fire motivational animation is presented. The various images 70-1 through 70-18 are stored in digital format in the image buffer of the processor 30. The images are stored in paired sets, each set of paired images shown in a separate one of FIGS. 7-15. The processor 30 determines which particular set of paired images is displayed in rapidly alternating fashion to form the animation displayed on the display screen 12 at any given time. Each paired set of images corresponds to a particular stage of attainment of the aforementioned goal values. The animation of water flow from the fireman's hose may be subdivided into a number of stages of achievement based on the scaled peak flow rate calculation expressed as % Expected PEF, for example five states as specified in the following Table I.

TABLE I

| Animation of water flow | Percent of expected PEF |
|---|---|
| Water State 1 | 0-19% |
| Water State 2 | 20-39% |
| Water State 3 | 40-59% |
| Water State 4 | 60-79% |
| Water State 5 | >=80% |

Similarly, the animation of extinguishment of the fire may be subdivided into a number of states of achievement based on the scaled total volume flow calculation expressed as % Expected FVC, for example three stages as specified in Table II following.

TABLE II

| Animation of fire | Percent of expected FVC |
|---|---|
| Fire State 2 | 40-59% |
| First State 1 | 60-79% |
| First State 0 | >=80% |

These fire extinguishment animation stages can only be reached after the test subject has attained the highest water flow stage, that is achieved a peak exhale flow rate during the test at least equal to the preset percentage, which in the described embodiment is 80%, of the goal value for the peak flow rate. Once the highest water flow stage has been reached, that water flow stage will be maintained throughout the remainder of the test, and the processor 30 will thereafter proceed to select the animation image to be displayed based of the fire stage for the remainder of the test.

Figure 8A:
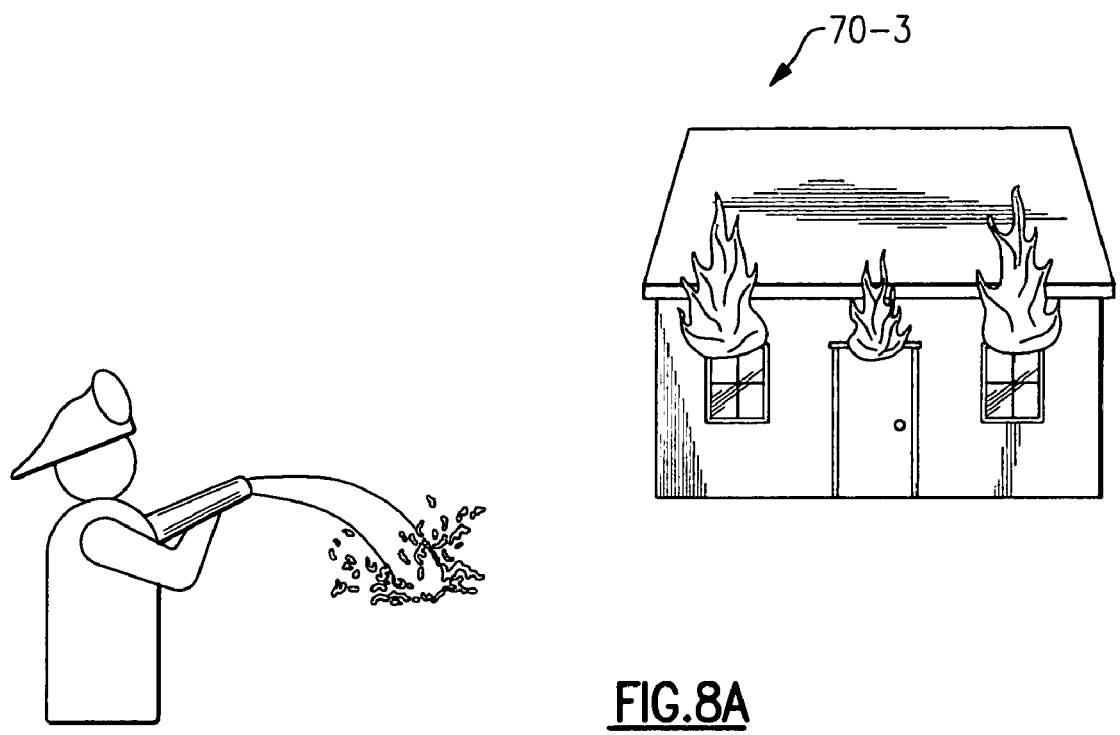
FIGS. 8A & 8B show a second set of paired animation images.
Figure 8B:
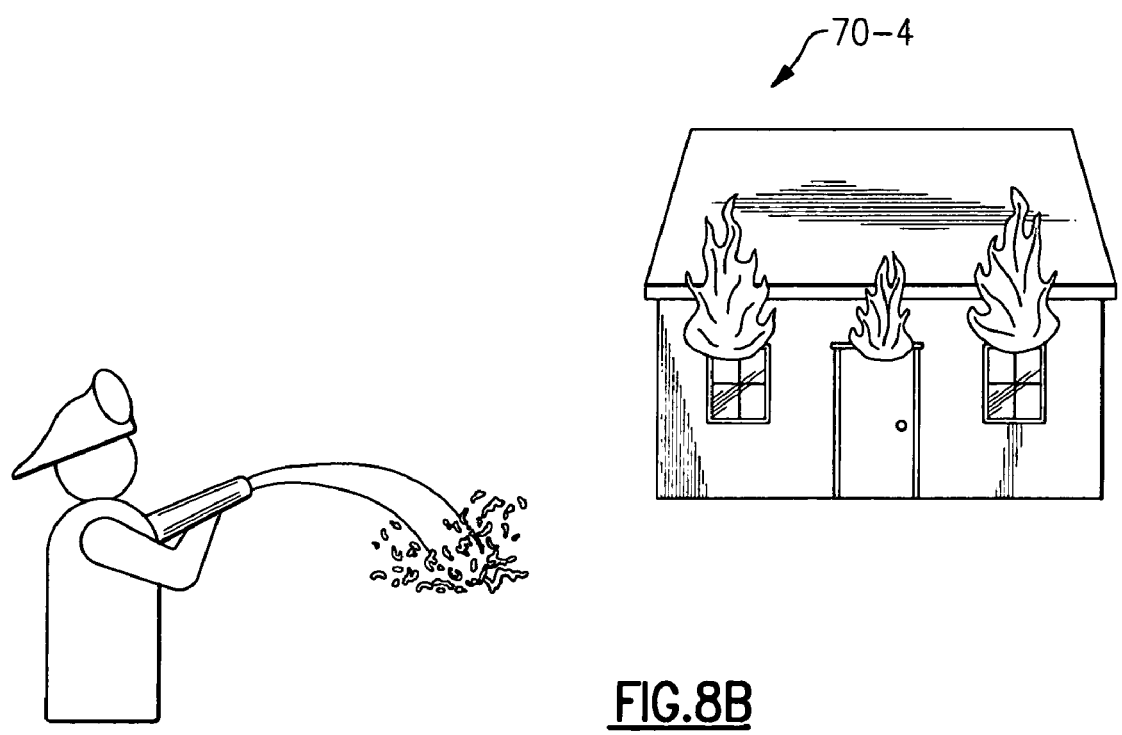
Figure 16:
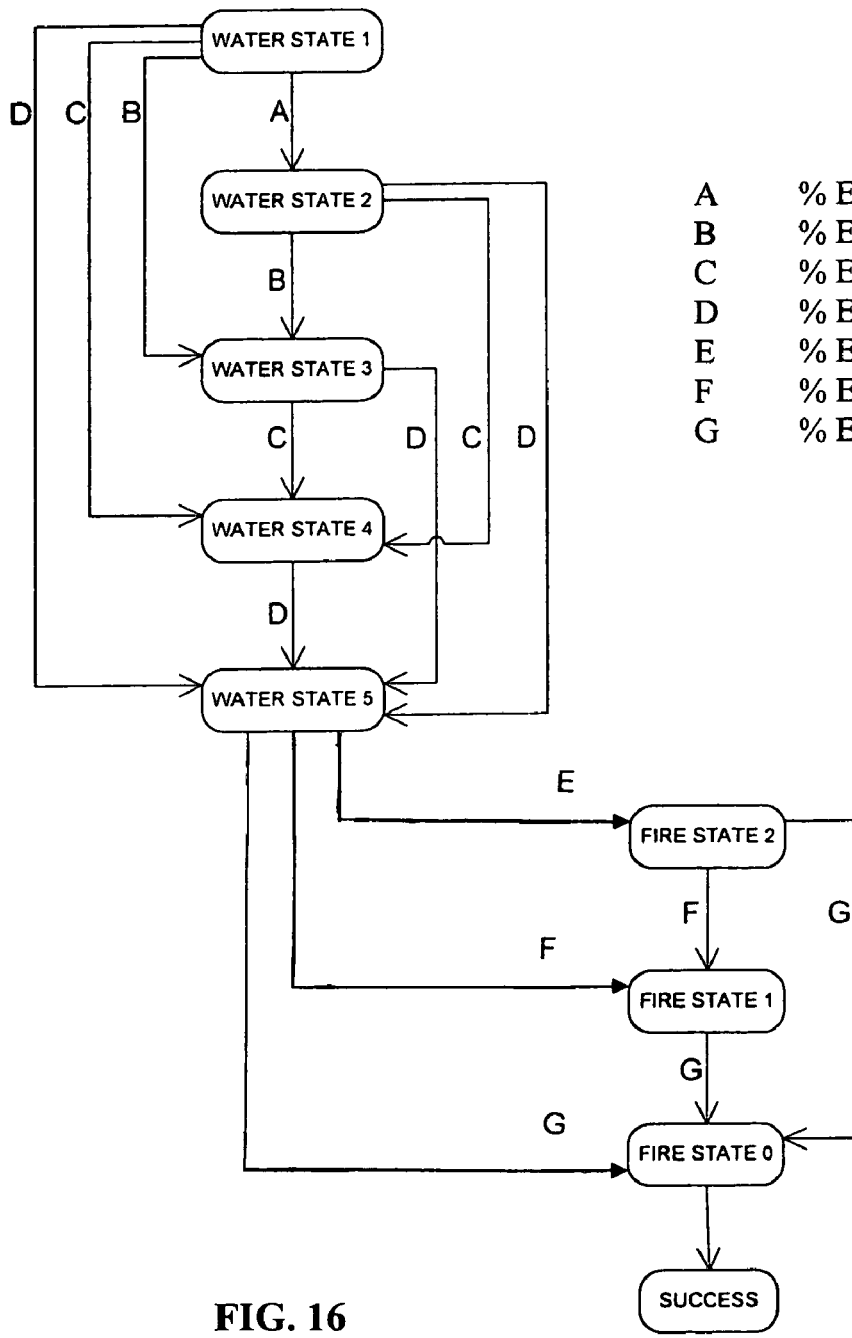
FIG. 16 is a flow chart illustrating the process for selection of the animation image to be displayed.

A block diagram illustrating the method of selecting the animation image is presented in FIG. 16. At the initiation of a test, the processor 30 will display paired animation images 70-1 and 70-2, shown in FIG. 7, which represent water state 1. By alternately displaying each image in a set of paired images in a rapid fashion, for example flipping between the paired images several times, for example 3 to 4 times, per second, a moving animation is created. This animation will continue to be displayed until the test subject achieves a scaled peak flow rate, % Expected PEF, of at least 20% of the goal value for PEF. Once that level of achievement is reached or exceeded, the processor 30 will change the animation image displayed to a new set of paired images based on the then current value of % Expected PEF. When the test subject achieves a current % Expected PEF lying in water state 2 as defined in Table I, the processor 30 will display paired animation images 70-3 and 70-4 as shown in FIG. 8.

Figure 9A:
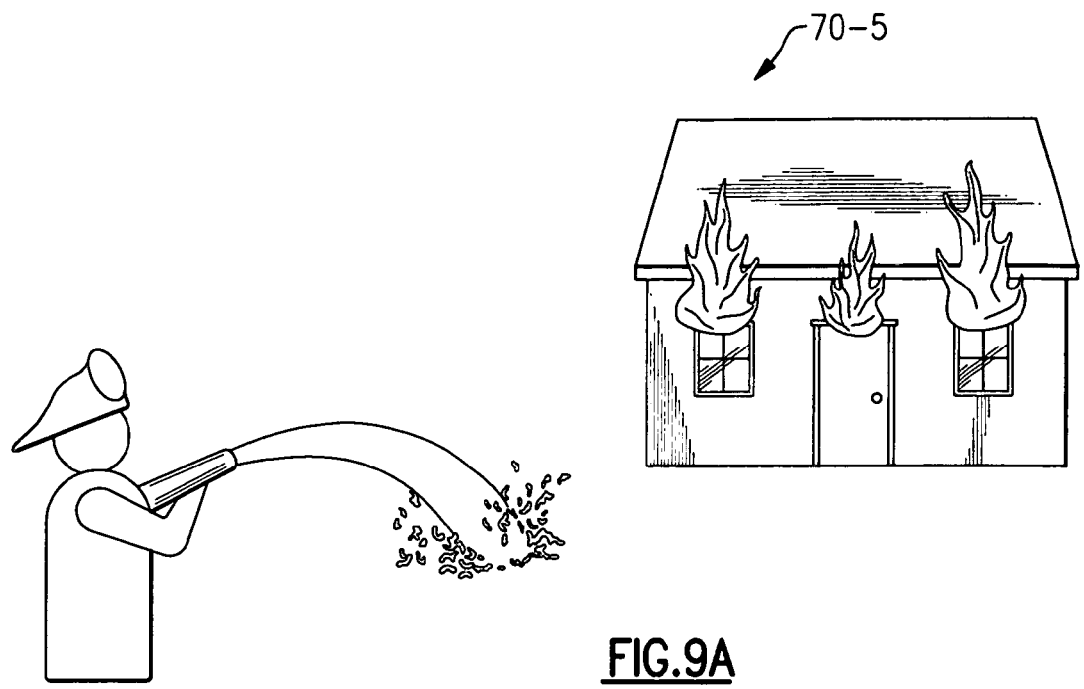
FIGS. 9A & 9B show a third set of paired animation images.
Figure 9B:
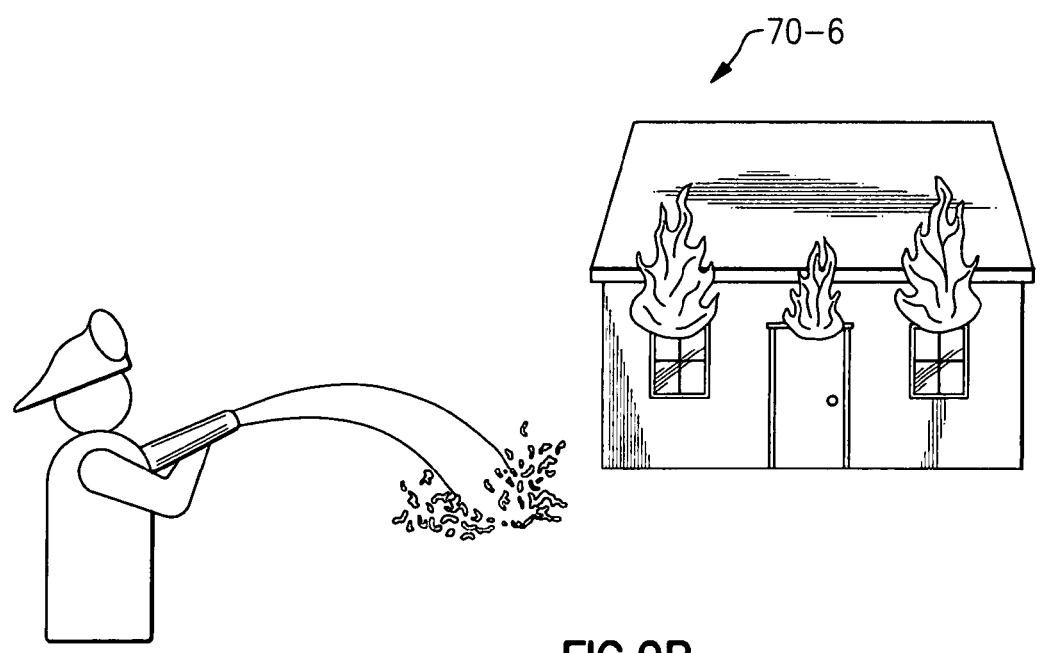
Figure 10A:
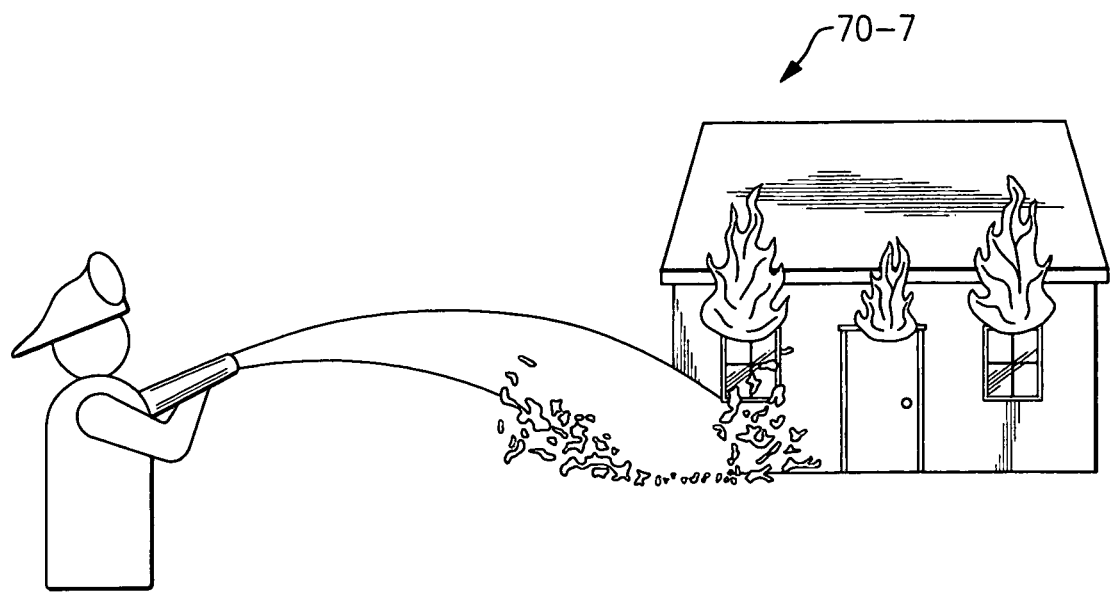
FIGS. 10A & 10B show a fourth set of paired animation images.
Figure 10B:
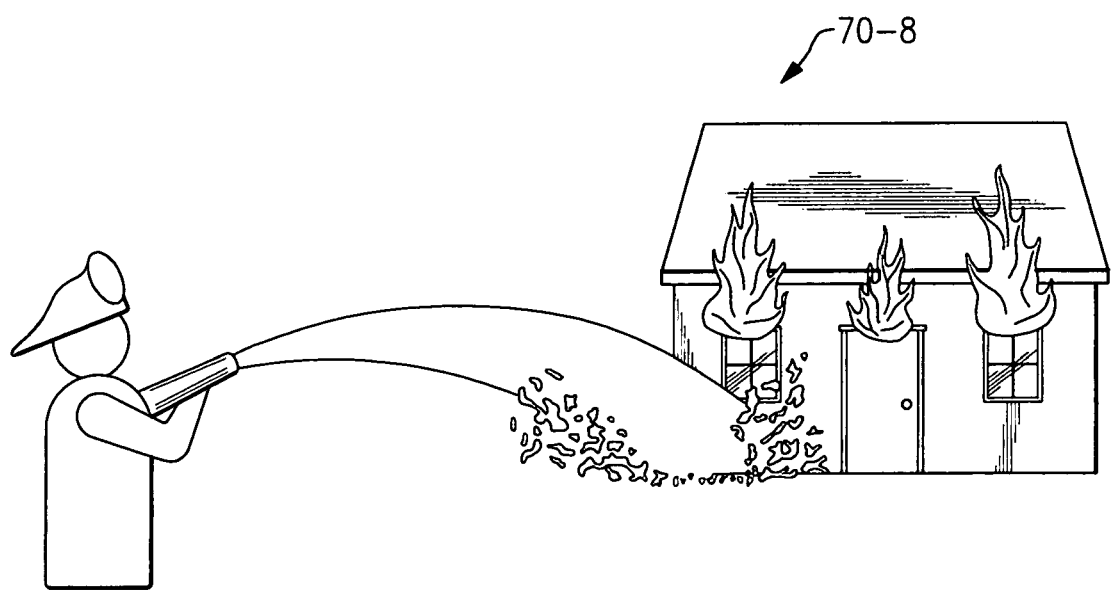
Figure 11A:
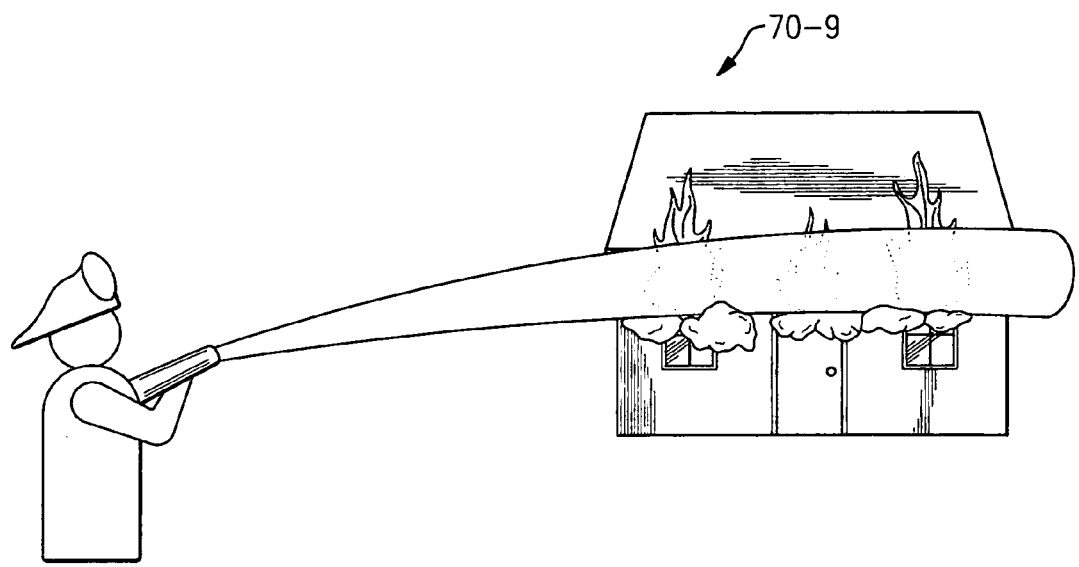
FIG. 11A & 11B show a fifth set of paired animation images.
Figure 11B:
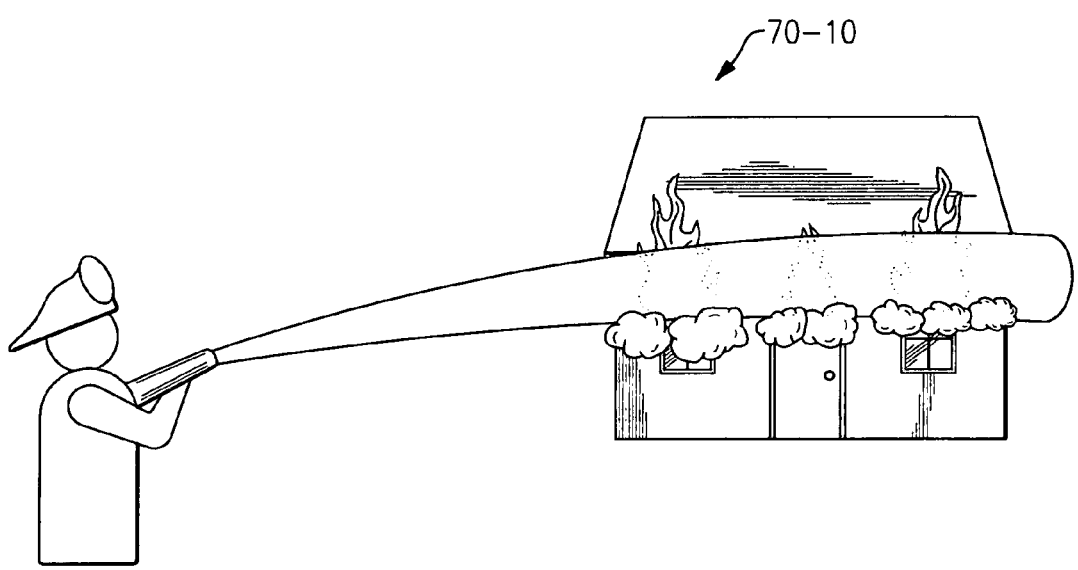

When the test subject achieves a current % Expected PEF lying in water state 3 as defined in Table I, the processor 30 will display paired animation images 70-5 and 70-6 as shown in FIG. 9. When the test subject achieves a current % Expected PEF lying in water state 4 as defined in Table I, the processor 30 will display paired animation images 70-7 and 70-8 as shown in FIG. 10. Eventually, when the test subject achieves a current % Expected PEF lying in water state 5 as defined in Table I, the processor 30 will display paired animation images 70-9 and 70-10 as shown in FIG. 11. At this point, the test subject will have exhaled hard enough to have reached at least 80% of the goal value for peak flow rate for that particular test subject and water from the hose will have finally reached the fire in the house.

Figure 12A:
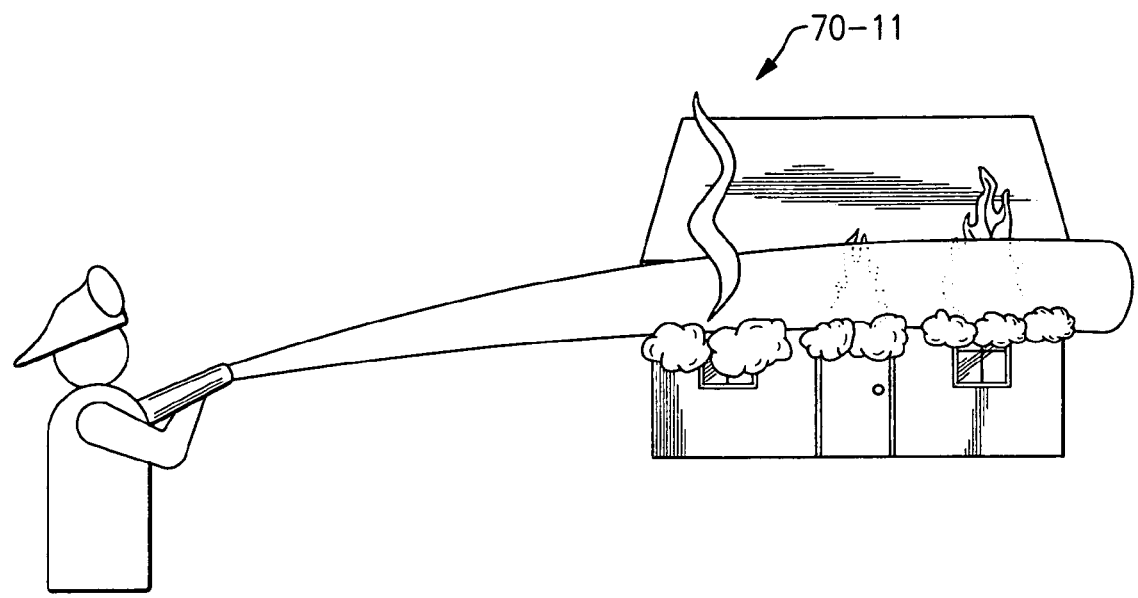
FIGS. 12A & 12B show a sixth set of paired animation images.
Figure 12B:
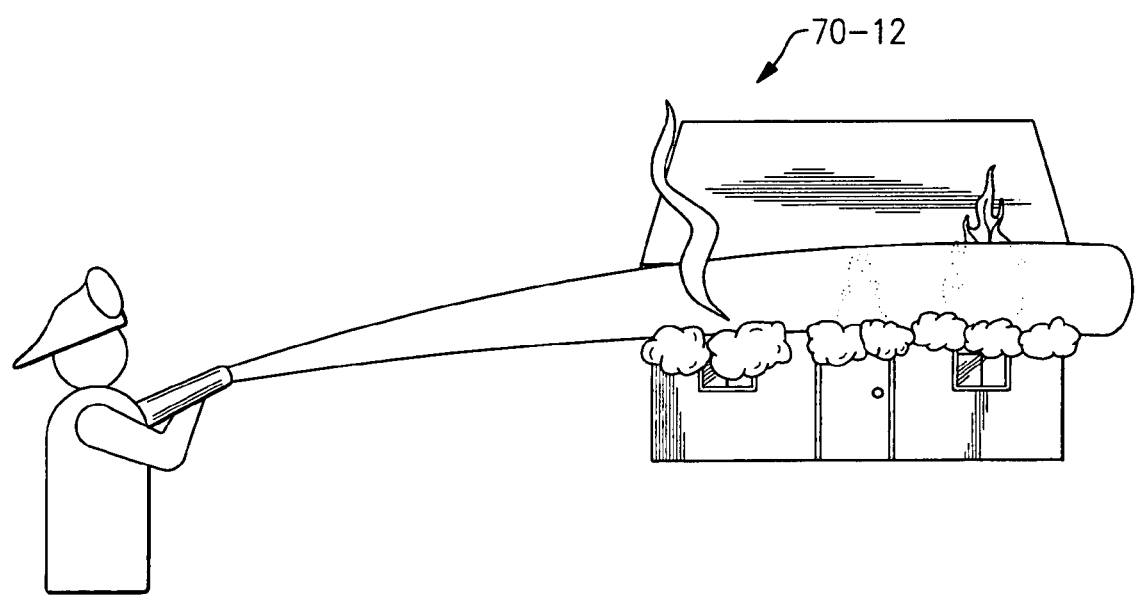
Figure 13A:
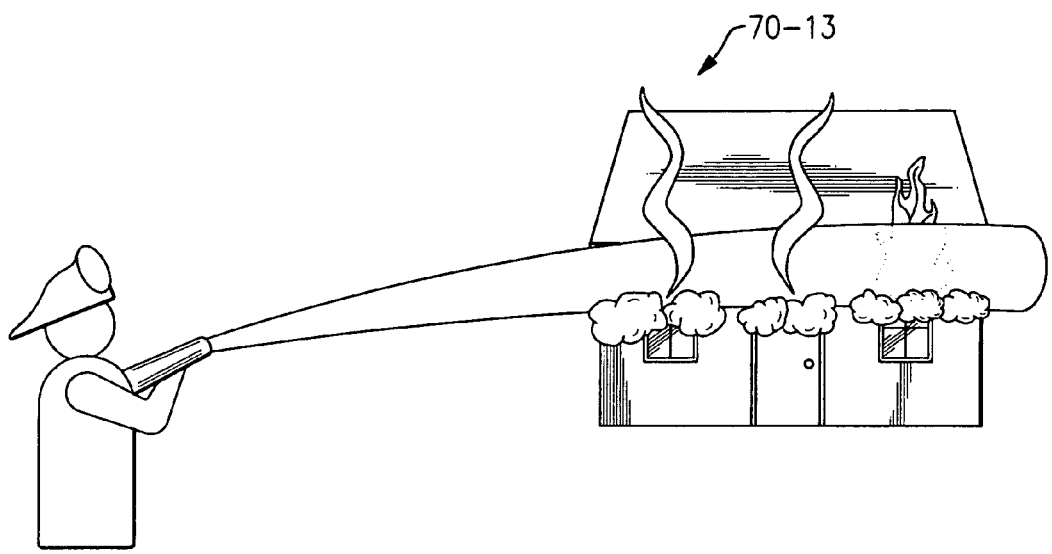
FIGS. 13A & 13B show a seventh set of paired animation images.
Figure 13B:
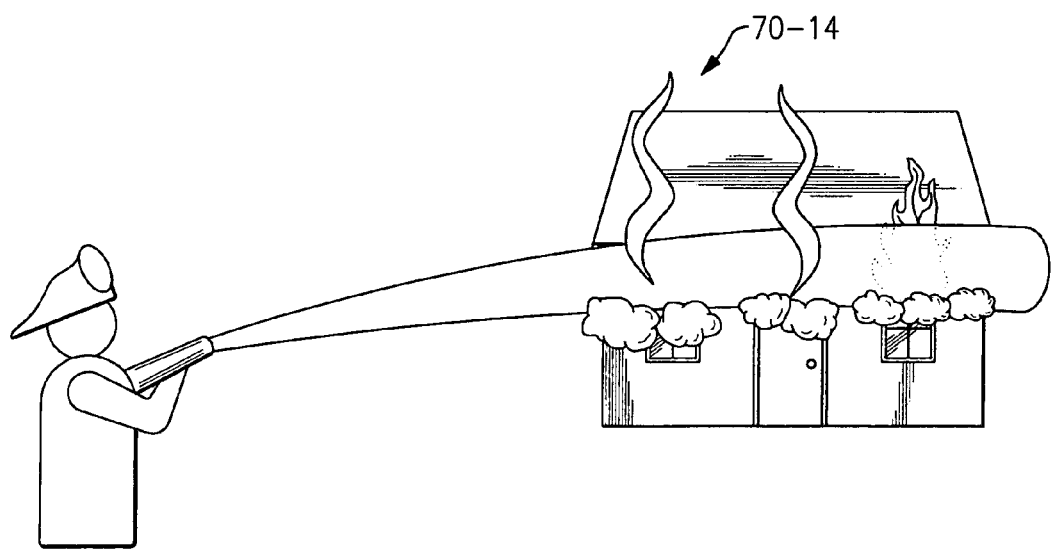
Figure 14A:
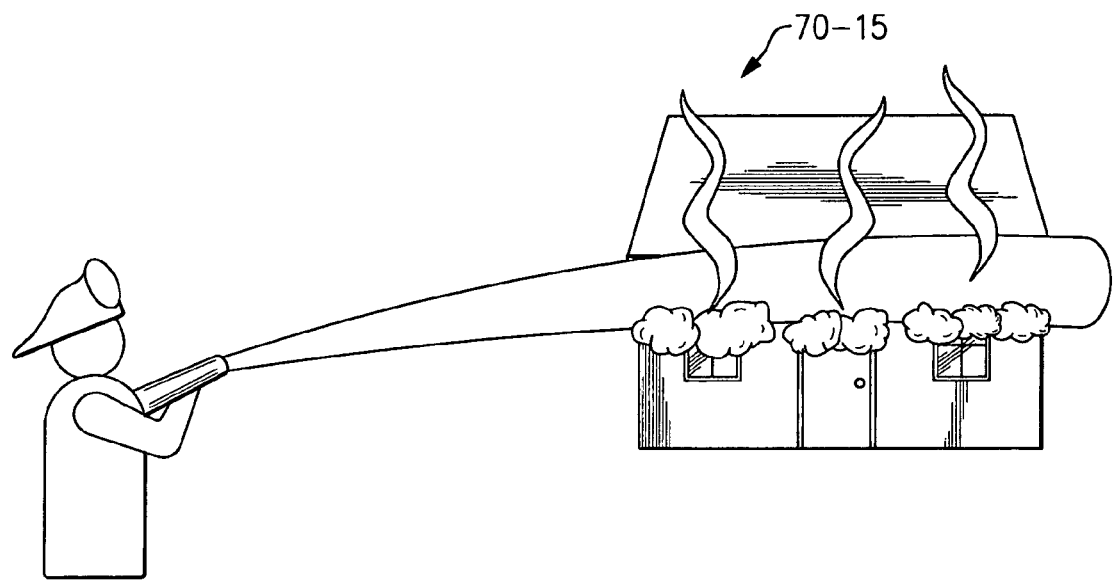
FIGS. 14A & 14B show a eighth set of paired animation images.
Figure 14B:
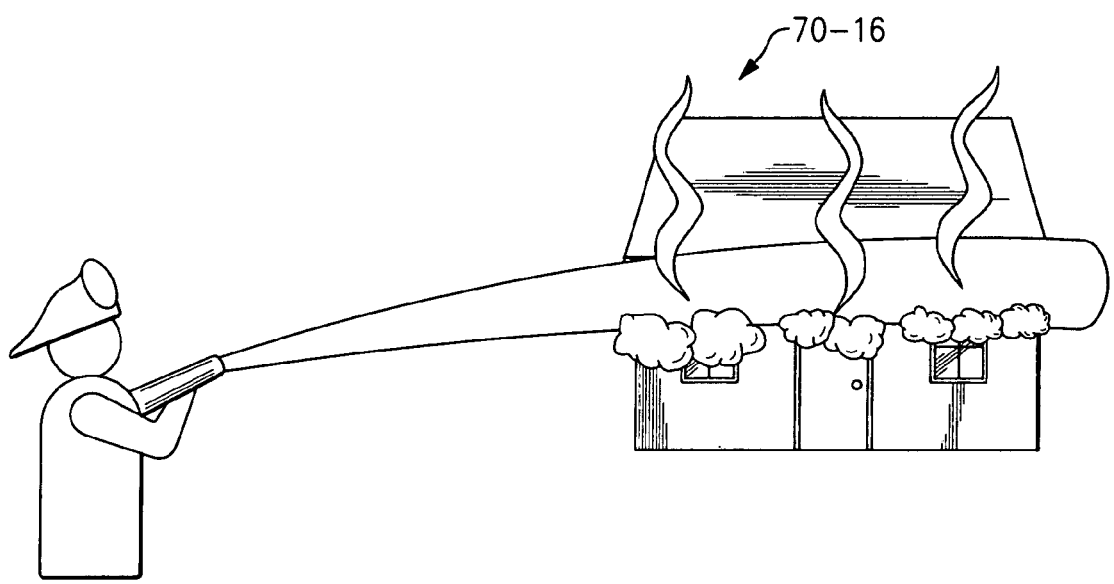
Figure 15A:
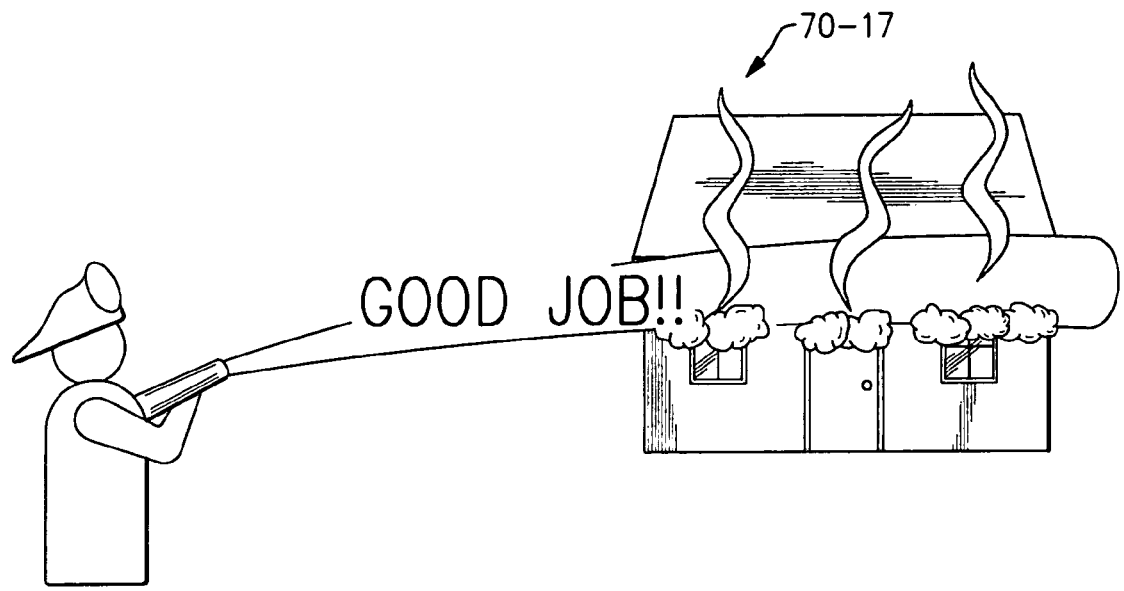
FIGS. 15A & 15B show a ninth set of paired animation images.
Figure 15B:
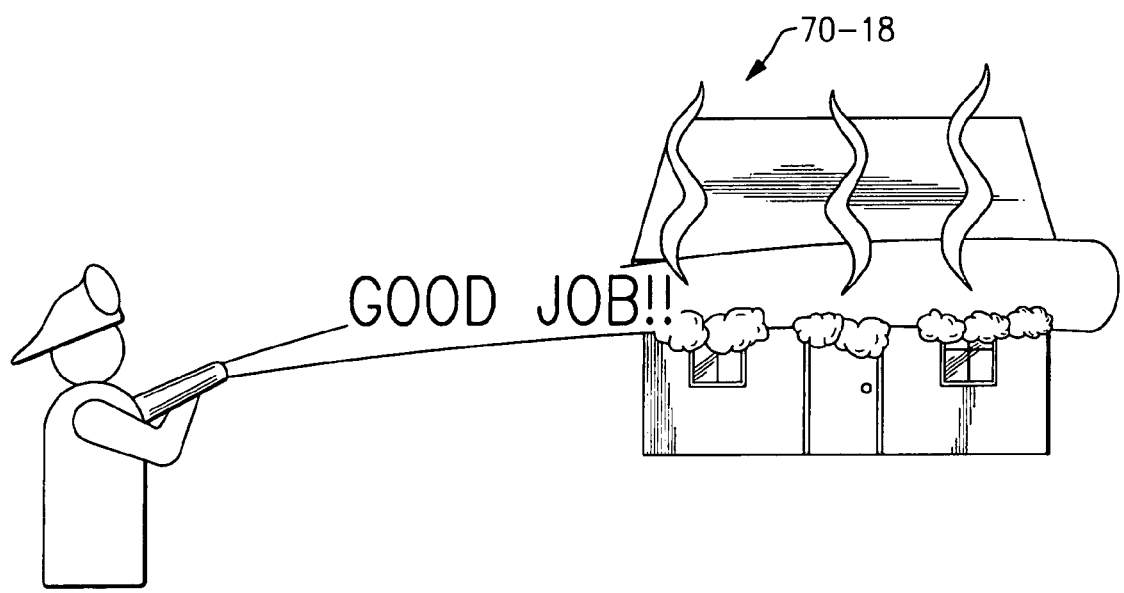

As seen in FIG. 11, although the water from the fireman's hose has reached the fires, none of the fires has been extinguished. For the remainder of the test, processor 30 will now use the fire state in selecting the animation image to be displayed. If the test has achieved a current scaled total volume flow, that is % Expected FVC, of at least 40% of the goal value for FVC for that test subject, the processor 30 will change the animation image to either fire state 2, fire state 1 or fire state 0 as appropriate. If the % Expected FVC corresponds to fire state 2 as defined in Table II, the processor 30 will display paired animation images 70-11 and 70-12 as shown in FIG. 12. If the % Expected FVC corresponds to fire state 1 as defined in Table II, the processor 30 will display paired animation images 70-13 and 70-14 as shown in FIG. 13. If the % Expected FVC corresponds to fire state 0 as defined in Table II, the processor 30 will display paired animation images 70-15 and 70-16 as shown in FIG. 14. Finally, the test subject has achieved both the peak flow rate goal and the total volume flow goal, the processor 30 will now display the final set of paired images 70-17 and 70-18, as shown in FIG. 15, with the congratulatory message "GOOD JOB".

The above-described relationship between the state of achievement and the animation image displayed is summarized in Table III.

TABLE III

| State | Animation Image | Description |
|---|---|---|
| Water State 1 | 70-1, 70-2 | Water drips out of hose<br>Three Flames on house |
| Water State 2 | 70-3, 70-4 | First increased water flow<br>Three fames on house |
| Water State 3 | 70-5, 70-6 | Second increased water flow<br>Three flames on house |
| Water State 4 | 70-7, 70-8 | Third increased water flow<br>Three flames on house |
| Water State 5 | 7-9, 7-10 | Water hits all flames<br>Three flames on house |
| Fire State 2 | 7-11, 7-12 | Leftmost flame turns to smoke<br>Middle and rightmost flames are still burning |
| Fire State 1 | 7-13, 7-14 | Middle flame turns to smoke<br>Rightmost flame is still burning |
| Fire State 0 | 7-15, 7-16 | Rightmost flame turns to smoke<br>All flames have been extinguished<br>Animation continues in this state until user input occurs |
| Success | 7-17, 7-18 | On user input, display "Good Job!" message if patient reached Fire State 0 |

It is to be understood that the operator of the spirometry apparatus may elect to display the achievement results of a test subject on a test in the conventional graphical format of FVC over time accompanied by a chart displaying the achieved values and the predicted values for various parameters including FVC and peak flow rate, as well as a percentage evaluation of the achieved value vis-à-vis its corresponding goal value.

The teachings of the present invention are not limited in application to the motivational animation of a fireman extinguishing a fire as depicted in the drawings. It is to be understood that the present invention may be practiced using other animations that include a first aspect that reflects a relative evaluation of a determined peak flow rate to a goal value therefor and a second aspect that reflects a relative evaluation of a determined total volume to a goal value therefor.

The method of the present invention has been described hereinbefore with reference to use of the spirometry system for evaluating a patient's expiration ability.

It is to be understood, however, that the teachings of the present invention may also be applied to use of spirometry system for evaluating a patient's inhalation ability. For example, in an inhalation test, the patient's peak inspiratory flow rate (PIF) would be measured rather than the patient's peak expiratory flow rate (PEF). For an inhalation evaluation, the animation images would, in accord with the teachings of the present invention, include a first aspect that reflects a relative evaluation of a determined inspiratory peak flow rate to a goal value therefor and a second aspect that reflects a relative evaluation of a determined total flow volume to a goal value therefor.

Although the invention has been described herein with reference to the embodiment of the spirometry system illustrated in the drawings and herein described, it is to be understood that the invention is not limited in application to that particular embodiment. Those skilled in the art will understand that the teachings of the invention may be readily applied to other embodiments of spirometry apparatus, some of which have already been alluded to hereinbefore, without departing from the spirit and scope of the following claims.

The invention claimed is:

1. A spirometry system comprising:
    an air tube defining a substantially linear air passage, said air tube adapted at one end to receive a flow of air that is exhaled by a user of said air tube;
    a sensor operatively associated with said air tube for measuring the exhaled air flow through said air tube;
    a processor operatively associated with said sensor for processing the exhaled air flow measurements from said sensor to determine a peak flow rate of the exhaled air and a total volume of the exhaled air flow through said air tube, evaluating said determined peak flow rate relative to a goal value therefor, evaluating said determined total volume relative to a goal value therefore, and generating a motivational animation for display to the user reflective of said evaluations; and
    a display operatively associated with said processor for displaying said motivational animation to the user, said animation providing incentive to encourage users of said apparatus to maximize their performance while using said apparatus, in which said animation is defined by a first aspect that presents a relative evaluation of a determined peak expiratory flow rate to a goal value therefor and a second aspect separate from said first aspect that presents a relative evaluation of a determined total flow volume to a goal value therefor, each of said first and second aspects being presented based on a common animation theme and wherein reaching each of said goal values of peak expiratory flow rate and total volume rate combine to produce a tangible result in said animation wherein the second aspect of the motivational animation is not presented until a target flow rate represented by said first aspect is first achieved.

2. A spirometry system as recited in claim 1 further comprising a user interface in operative association with said processor whereby data may be selectively input to said processor.

3. A spirometry system as recited in claim 1, wherein the motivational animation is represented as a firehose putting out a fire in which the first aspect is represented by an animated representation of water from said hose and the second aspect is represented by an animated representation of water striking the fire to extinguish the fire wherein meeting the first goal value is required before any of the fire can be extinguished.

4. A spirometry system as recited in claim 3, wherein meeting each of said goal values of said first and second aspects is required to extinguish the fire.

* * * * *